United States Patent [19]

Guyton et al.

[11] Patent Number: 4,527,057
[45] Date of Patent: Jul. 2, 1985

[54] TEST BODY ARRANGEMENT

[75] Inventors: Peter F. Guyton, Elstree; Albert H. R. Lonn, St. Albans, both of England

[73] Assignee: General Electric Company, Milwaukee, Wis.

[21] Appl. No.: 452,186

[22] Filed: Dec. 22, 1982

[30] Foreign Application Priority Data

Dec. 23, 1981 [GB] United Kingdom ............... 8138716

[51] Int. Cl.$^3$ ............................................. G01D 18/00
[52] U.S. Cl. .................................. 250/252.1; 378/207
[58] Field of Search ............ 250/361 R, 363 S, 252.1; 378/207

[56] References Cited

U.S. PATENT DOCUMENTS 4,126,789 11/1978 Yogl et al. ..................... 378/207
4,280,047 7/1981 Enos ............................. 250/252.1

FOREIGN PATENT DOCUMENTS 168579 12/1981 Japan ............................. 378/207

OTHER PUBLICATIONS

"Phantoms for Cameras & Scanners", product data brochure from Atomic Development Corp., Plainview, N.Y., 1976.

Primary Examiner—Janice A. Howell
Attorney, Agent, or Firm—Douglas E. Stoner; Alexander M. Gerasimow

[57] ABSTRACT

A test body or phantom for use in checking the performance of apparatus which detects the emission of radiations from a body includes an element of predetermined shape which incorporates a material having a known level of radiation intensity.

6 Claims, 4 Drawing Figures

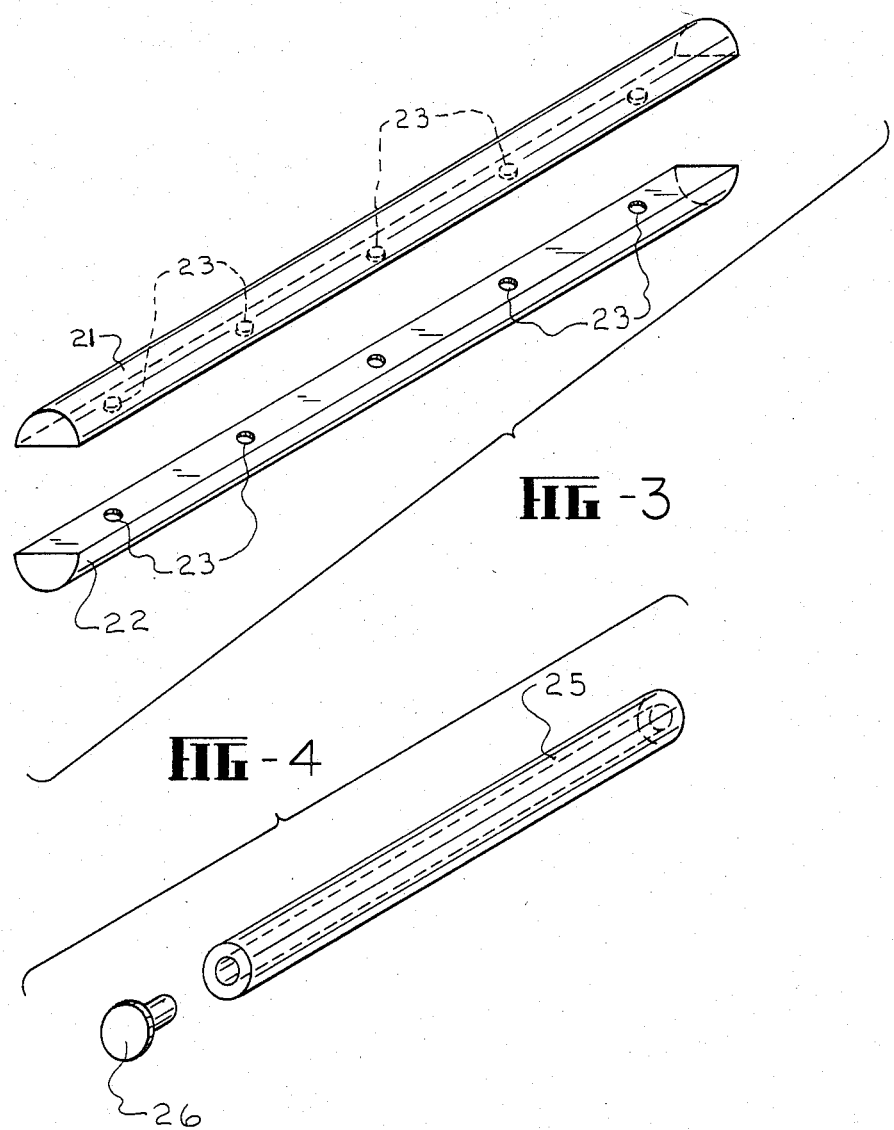

TEST BODY ARRANGEMENT

BACKGROUND OF THE INVENTION

This invention relates to a test body arrangement (otherwise known as a Test Phantom) for use in checking the performance of apparatus which detects the emission of radioactive radiations from a body by means of a detector assembly positioned at a given distance from the body. The detector assembly consists, in one embodiment, of a radiation sensitive element which extends over an area in a plane. Such a detector assembly produces a planar image which may be in the form of a matrix arranged in rows and columns, suitable for subsequent computer processing. It is, of course, possible for the detector assembly to be arranged in other than a plane, for example the assembly could be arranged on a curve about a longitudinal axis of the body from which the radiations are detected. Furthermore, the detector assembly may be so mounted that it can be rotated about the body. The planar views obtained by the detector assembly at various incremental positions around the body may be reconstructed to form transaxial sectional views of that body.

One form of phantom or test body arrangement for testing the operating characteristics of a tomographic analytical apparatus is described in U.S. Pat. No. 4,055,771. The embodiments described therein disclose the use of X-ray energy absorption means which are arranged in a predetermined configuration within the body and which include a fluid bath chamber.

SUMMARY OF THE INVENTION

In its preferred embodiment, the present invention provides a test body or phantom having at least one element of a given shape inserted in the body in a particular position, the element incorporating a material which has a known level of radiation intensity, whereby a test body can be assembled giving a predetermined radiation pattern.

BRIEF DESCRIPTION OF THE DRAWINGS

Embodiments of test bodies in accordance with the invention will now be described, by way of example, with reference to the accompanying drawings in which:

FIGS. 2, 3 and 4 are perspective exploded views of elements for insertion in the body shown in FIG. 1.

DETAILED DESCRIPTION OF THE INVENTION

Figure 1:
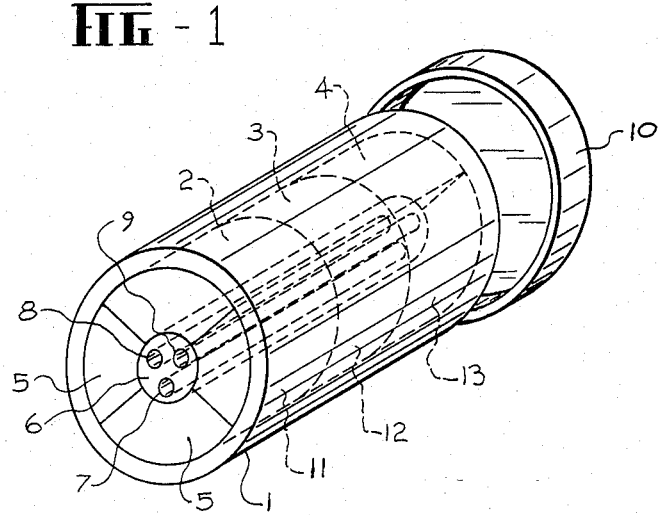
FIG. 1 is a perspective view of a test body or test phantom with its lid shown separated.

Referring to FIG. 1, there is shown at 1 an outer tubular transparent casing of a plastics material, for example Perspex, within which there are arranged three sets 2, 3 and 4 of part-quarter segments 5. Each set of segments 2, 3 and 4 forms a distinct tubular band. None of the segments 5 extends to the centre of the assembly and a central tubular region contains a rod 6 having longitudinally extending holes 7, 8 and 9 therein.

The segments 5 are made of a moulded plastics material and the segments of each set incorporate both a colouring material which is distinctive for that set and a radioactive material which emits gamma rays, the intensity of the gamma radiations emitted from one set being of a known level which is different from that emitted by each of the other sets. Since each of the segments 5 is of the same shape, it is possible for one or more of the segments of one set, having a particular radiation level, to be interchanged with segments of one or more of the other sets. As a result of such an interchange of the segments it is possible to provide a body whose radiation intensity varies not only in bands 11, 12 and 13 corresponding to the original sets 2, 3 and 4, along its length, but with radiation intensity which varies around the circumference of each of the bands. It is furthermore possible to vary the pattern of radiation intensity emitted by including one or more segments 5 which is not loaded with radioactive material.

Furthermore, by loading into the holes 7, 8 and 9, rods having varying levels of radiation emission, varying levels of radiation emission along their length, or emitting no radiation at all, it is possible to simulate varying degrees of radiation patterns in which one source of radiation is at a different depth from another in a particularly simple way.

The rods to be loaded into holes 7, 8 and 9 will commonly be tubular and made of a solid plastics material, for example Perspex, loaded evenly throughout with a radioactive material, for example cobalt 57, so that a uniform distribution of radiation is obtained from the rods.

Figure 2:
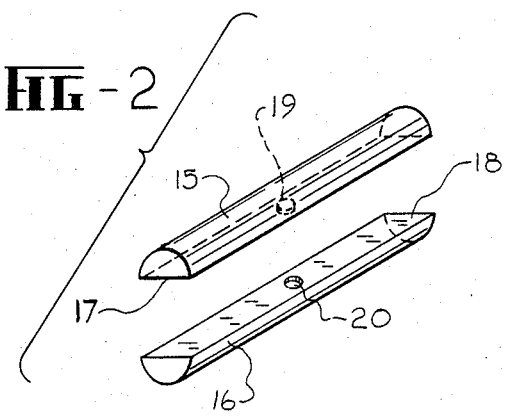

A modification of this form of rod is shown in FIG. 2 to comprise two similar parts 15 and 16, of solid plastics material which have respective flat faces 17 and 18. Each of the parts 15 and 16 includes a recess 19 or 20 in a respective one of the faces 17 and 18, so that, when the faces 17 and 18 are placed together a rod is created for insertion into one of the holes 7, 8 or 9 having a central space formed by the recesses 19 and 20. The rod which is created in the arrangement of FIG. 2 extends into one of the holes 7, 8 or 9 through only the first set of segments 2. The solid material of which the parts 15 and 16 are made is not radioactive and the arrangement shown in FIG. 2 is used by placing a small radioactive point source element in the central space formed by the recesses 19 and 20 before the assembly consisting of the two parts 15 and 16 is placed in one of the holes 7, 8 or 9 and the test body or phantom is used for resolution measurements.

Referring now to FIG. 3, there is shown a form of rod constituted by two parts 21 and 22, similar to the parts 15 and 16 shown in FIG. 2, but having a greater length so that the rod which is created by placing them together extends through the three sets of segments 2, 3 and 4. The parts 21 and 22 each have a series of equally spaced recesses 23, pairs of which form a series of spaces each able to contain a point source element, thereby enabling upon insertion of the rod into the body a phantom to be provided which can be used to test both the longitudinal and the spatial resolution of the array.

Referring to FIG. 4, there is shown a hollow tubular insert 25 of non-radioactive material having a plug 26. Radioactive liquid of known strength can be introduced into the tubular insert 25 and retained by the plug 26, thereby providing a further form of insert for use in a phantom to enable quantitive measurements to be made.

The present invention enables a number of different combinations of radiation pattern to be produced, each of which can be assembled easily and be used as a standard for testing the performance of apparatus in relation to each of a number of quite different applications.

It will be appreciated that variations of and modifications in the embodiments described can be made within the scope of the present invention. For example, in the arrangement of FIG. 1 the elements to be inserted in the longitudinally extending holes 7, 8 and 9 can be located on the lid 10 and be inserted as the lid 10 is clamped onto the body 1. It will also be appreciated that, although the segments 5 in the particular embodiment shown in FIG. 1 are all similar, it would be within the scope of the invention to employ more than one shape of segment. It would for example be possible to have a segment which extended over one half of the area of the casing 1 instead of only one quarter, or a segment which extended between two of the bands 11, 12 or 13.

Furthermore the outer casing 1, or yet another separate outer casing, may have an elliptical cross-section such that it represents more closely the cross-section of a human being.

Other variations and modifications will be apparent to those skilled in the art.

We claim:

1. A test body for use in checking the performance of apparatus which detects the emission of radiation from a body, the test body comprising an outer tubular casing having disposed therein at least a pair of longitudinally spaced bands of material, each of said bands comprising a plurality of segments with each of said segments having a known level of radiation intensity being incorporated therein.

2. A test body as claimed in claim 1 including first and second bands of said segments, the segments of the first band each incorporating a material having one level of radiation intensity and the segments of the second band incorporating a material having a second level of radiation intensity.

3. A test body as claimed in claim 1 having first and second bands of said segments, wherein segments having one level of radiation intensity and segments having another level of radiation are both arranged in each of the said bands.

4. A test body as claimed in claim 1 including an axially extending first rod and a longitudinally extending second rod arranged within the first rod, the second rod incorporating a radioactive material having a known level of radiation intensity.

5. A test body as claimed in claim 4 including a pair of similar parts of semi-circular cross section constituting the second rod, at least one of said parts defining a recess for a radioactive element.

6. A test body as claimed in claim 1 including an axially extending rod, and a tubular insert for a radioactive liquid within the rod.

* * * * *